United States Patent [19]
Collier, Jr.

[11] Patent Number: 5,314,499
[45] Date of Patent: May 24, 1994

[54] ARTIFICIAL LIMB INCLUDING A SHIN, ANKLE AND FOOT

[76] Inventor: Milo S. Collier, Jr., 1152 Douglas St., Longview, Wash. 98632

[21] Appl. No.: 680,310

[22] Filed: Apr. 4, 1991

[51] Int. Cl.⁵ .......................... A61F 2/64; A61F 2/74; A61F 2/66; A61F 2/68
[52] U.S. Cl. ...................... 623/47; 623/27; 623/50; 623/51; 623/53
[58] Field of Search ............ 623/35, 28, 40, 27, 623/47, 53, 32, 50, 51, 55

[56] References Cited

U.S. PATENT DOCUMENTS

| | | |
|---|---|---|
| 507,453 | 10/1893 | Read . |
| 579,009 | 3/1897 | Richen . |
| 584,004 | 6/1897 | Lyons . |
| 598,230 | 2/1898 | Roberts et al. . |
| 640,540 | 1/1900 | Daniels . |
| 667,511 | 2/1901 | Fenner et al. ......................... 623/47 |
| 692,719 | 2/1902 | Seeley .................................. 623/55 |
| 714,052 | 11/1902 | Staggs .................................. 623/53 |
| 810,180 | 1/1906 | Wintermute ........................... 623/55 |
| 959,881 | 5/1910 | Price .................................... 623/55 |
| 963,797 | 7/1910 | Mueller ................................. 623/52 |
| 1,023,247 | 4/1912 | Frees .................................... 623/51 |
| 1,090,327 | 3/1914 | Milligan . |
| 1,151,520 | 8/1915 | Hanger . |
| 1,279,356 | 9/1918 | Kenney . |
| 1,294,632 | 2/1919 | Dickson . |
| 1,319,471 | 10/1919 | Giebeler-Wanke ............... 623/35 X |
| 1,698,372 | 1/1929 | McElroy . |
| 1,804,915 | 5/1931 | Collins . |
| 1,995,412 | 3/1935 | Wolfe . |
| 2,036,830 | 4/1936 | Rowley . |
| 2,126,654 | 8/1938 | Morris . |
| 2,130,271 | 9/1938 | Eastham . |
| 2,197,093 | 4/1940 | Campbell . |
| 2,289,154 | 7/1942 | Van Cise . |
| 2,416,817 | 3/1947 | Carter . |
| 2,442,151 | 5/1948 | Strickland . |
| 2,443,356 | 6/1948 | Mathis . |
| 2,446,042 | 7/1948 | Valenti . |
| 2,453,969 | 11/1948 | Carter . |
| 2,465,771 | 3/1949 | Weaver . |
| 2,470,480 | 5/1949 | Fogg . |
| 2,472,819 | 6/1949 | Giesen . |

(List continued on next page.)

FOREIGN PATENT DOCUMENTS

| | | | |
|---|---|---|---|
| 0690957 | 9/1930 | France ................................. 623/27 |
| 0605613 | 5/1978 | U.S.S.R. ............................... 623/51 |
| 1567202 | 5/1990 | U.S.S.R. . |

OTHER PUBLICATIONS

"Copes/Bionic Ankle" Nov. 1985.

*Primary Examiner*—Randall L. Green
*Assistant Examiner*—Dinh X. Nguyen
*Attorney, Agent, or Firm*—Kolisch Hartwell Dickinson McCormack & Heuser

[57] ABSTRACT

The invented artificial limb includes a shin, ankle and foot. The shin includes a first mount, a second mount positioned below the first mount, and a plurality of rods extending between the first and second mounts, where at least one rod is a load bearing rod. The foot includes an elongate member having a toe section and a heel section. In many applications, the elongate member is arched. The shin is coupled to the foot by an ankle. The ankle allows the shin to rotate around an axis substantially perpendicular to a line between the toe and heel sections of the foot. A rotation controlling element such as an elastic band or a compression spring is connected to both the ankle and to the elongate member to restrict rotation of the shin toward the heel section of the foot. The ankle may also allow the shin to move around a second axis to simulate lateral rotation of the ankle. In the preferred embodiment, the rods of the shin and the elongate member of the foot are flexible to provide a more comfortable and responsive artificial limb.

15 Claims, 6 Drawing Sheets

U.S. PATENT DOCUMENTS

| | | | |
|---|---|---|---|
| 2,475,372 | 7/1949 | Catranis . | |
| 2,475,373 | 7/1949 | Catranis . | |
| 2,490,806 | 12/1949 | Henschke et al. . | |
| 2,542,436 | 2/1951 | Schultz . | |
| 2,545,146 | 3/1951 | Hydorn . | |
| 2,551,724 | 5/1951 | Campbell . | |
| 2,570,735 | 10/1951 | Weise . | |
| 2,605,475 | 8/1952 | Burger et al. . | |
| 2,620,485 | 12/1952 | Greissinger . | |
| 2,644,165 | 7/1953 | Grisoni . | |
| 2,687,533 | 8/1954 | McCormick . | |
| 2,692,392 | 10/1954 | Bennington et al. . | |
| 2,699,554 | 1/1955 | Comelli . | |
| 2,731,645 | 1/1956 | Woodall | 623/35 X |
| 2,745,108 | 5/1956 | Withers . | |
| 3,400,408 | 10/1964 | Garcia | 623/55 |
| 3,480,972 | 12/1969 | Prahl | 623/35 X |
| 3,551,914 | 1/1971 | Woodall | 623/35 X |
| 3,754,286 | 8/1973 | Ryan . | |
| 3,776,569 | 10/1973 | Orange . | |
| 3,874,004 | 4/1975 | May . | |
| 3,982,280 | 9/1976 | Asbelle et al. . | |
| 4,007,497 | 2/1977 | Haupt . | |
| 4,089,072 | 5/1978 | Glabiszewski | 623/27 |
| 4,177,525 | 12/1979 | Arbogast et al. . | |
| 4,180,872 | 1/1980 | Chaikin . | |
| 4,216,550 | 8/1980 | Thompson | 623/38 |
| 4,328,594 | 5/1982 | Campbell et al. . | |
| 4,360,931 | 11/1982 | Hampton . | |
| 4,364,128 | 12/1982 | Mummert . | |
| 4,446,580 | 5/1984 | Furuya et al. . | |
| 4,547,913 | 10/1985 | Phillips . | |
| 4,605,417 | 8/1986 | Fleischauer | 623/49 |
| 4,619,661 | 10/1986 | Axelsson . | |
| 4,636,220 | 1/1987 | Ziegelmeyer . | |
| 4,645,509 | 2/1987 | Poggi et al. | 623/55 |
| 4,652,266 | 3/1987 | Truesdell . | |
| 4,721,510 | 1/1988 | Cooper et al. | 625/55 |
| 4,764,172 | 8/1988 | McCoy | 623/52 X |
| 4,822,363 | 4/1989 | Phillips . | |
| 4,865,612 | 9/1989 | Arbogast et al. . | |
| 4,883,493 | 11/1989 | Martel et al. | 623/38 |
| 4,892,553 | 1/1990 | Prahl . | |
| 4,911,724 | 3/1990 | Fikes . | |
| 4,938,776 | 7/1990 | Masinter . | |
| 4,959,073 | 9/1990 | Merlette . | |
| 5,019,109 | 5/1991 | Voisin | 623/55 X |
| 5,062,859 | 11/1991 | Naeder | 625/55 |
| 5,139,525 | 8/1992 | Kristinsson | 623/55 |

ARTIFICIAL LIMB INCLUDING A SHIN, ANKLE AND FOOT

TECHNICAL FIELD

This invention relates to prosthetic devices and more particularly to a shin, ankle and foot prosthesis for lower extremity amputees.

BACKGROUND ART

A prosthetic device or prosthesis is an artificial substitute for a missing part of the body such as a limb. Numerous different prostheses have been developed, each trying to replicate the function and appearance of the replaced body part.

Lower leg prostheses present unique problems. They must be strong enough to support the weight of a person and to withstand the forces encountered when walking or running. But they must also be light enough so that they can be used comfortably. Additionally, an increasing number of lower-limb amputees desire to participate in athletic activities. Thus, lower leg prostheses must be strong enough to accommodate athletic activity while remaining comfortable to the user. The invented artificial limb addresses those problems.

DISCLOSURE OF THE INVENTION

The invented artificial limb includes a shin, ankle and foot. The shin includes a first mount, a second mount positioned below the first mount, and a plurality of rods extending between the first and second mounts, where at least one rod is a load bearing rod. The foot includes an elongate member having a toe section and a heel section. In many applications, the elongate member is arched. The shin is coupled to the foot by an ankle. The ankle allows the shin to rotate around an axis substantially perpendicular to a line between the toe and heel sections of the foot. A rotation controlling element such as an elastic band or a compression spring is connected to both the ankle and to the elongate member to restrict rotation of the shin toward the heel section of the foot. The ankle may also allow the shin to move around a second axis to simulate lateral rotation of the ankle. In the preferred embodiment, the rods of the shin and the elongate member of the foot are flexible to provide a more comfortable and responsive artificial limb.

DETAILED DESCRIPTION AND BEST MODE FOR CARRYING OUT THE INVENTION

Figure 1:
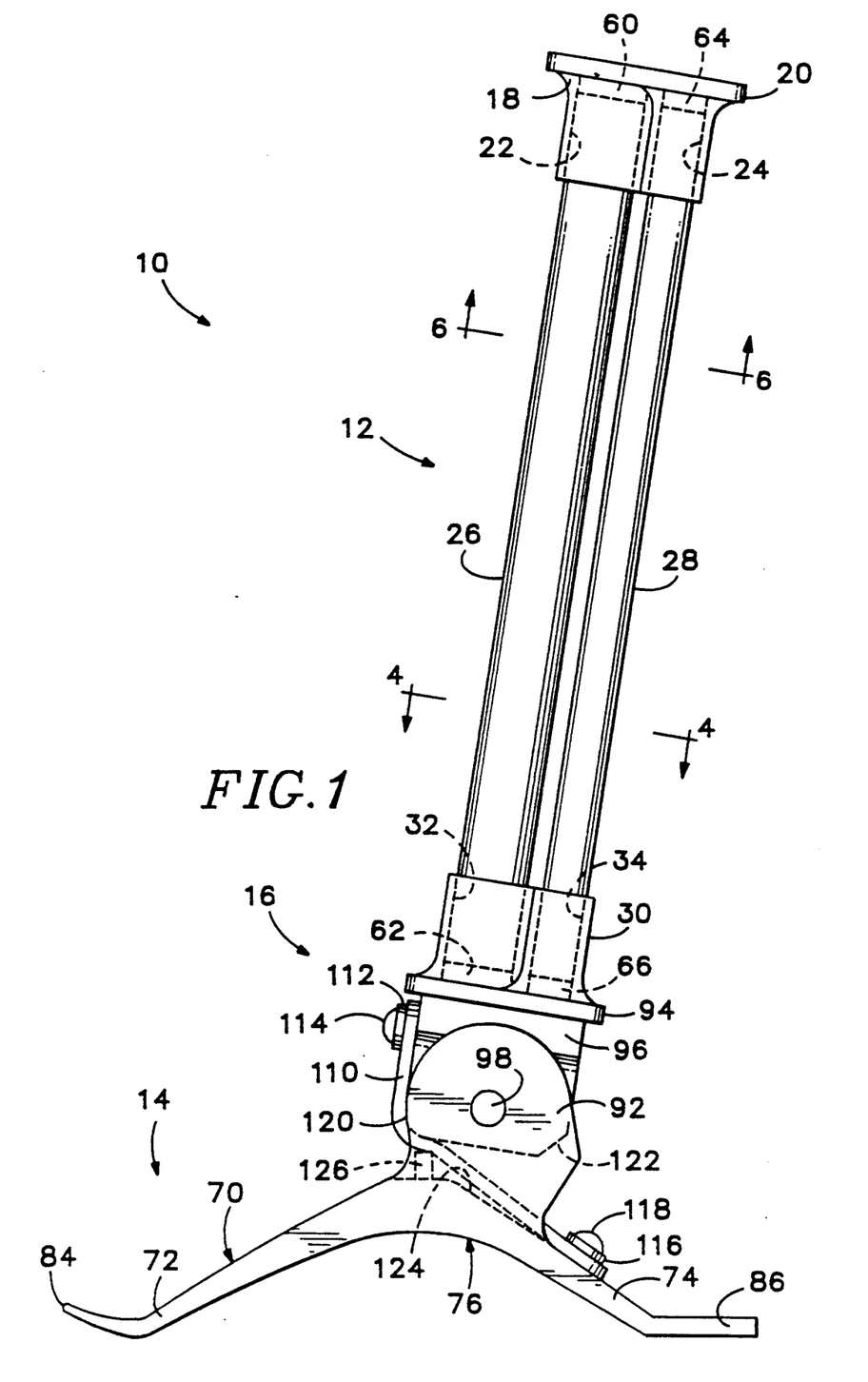
FIG. 1 is a side plan view of the invented artificial limb.
Figure 2:
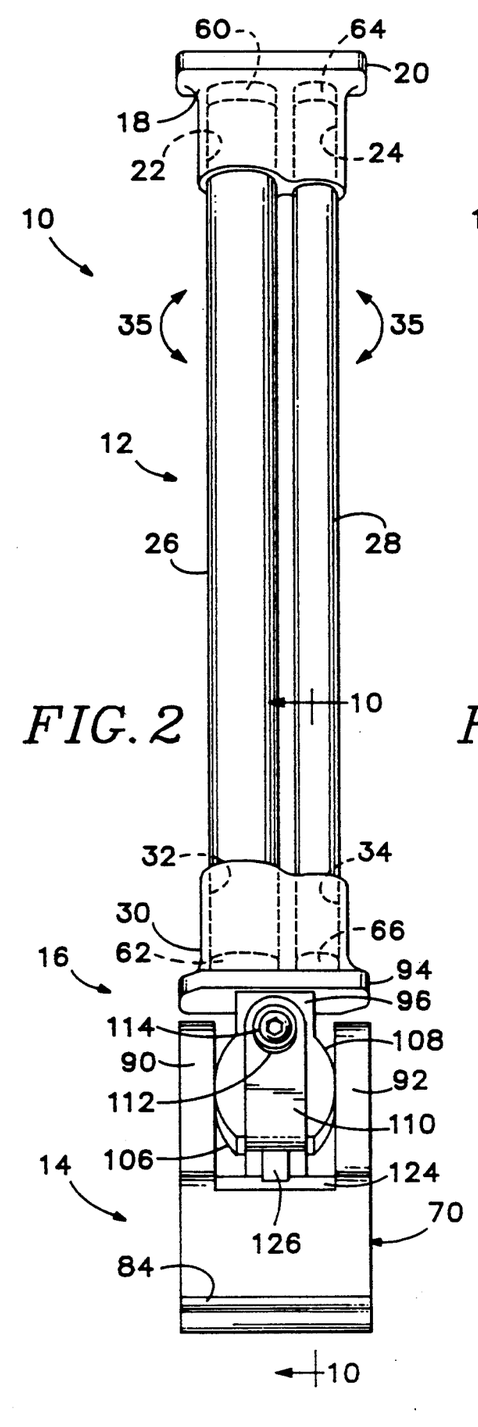
FIG. 2 is a front plan view of the invented limb.
Figure 3:
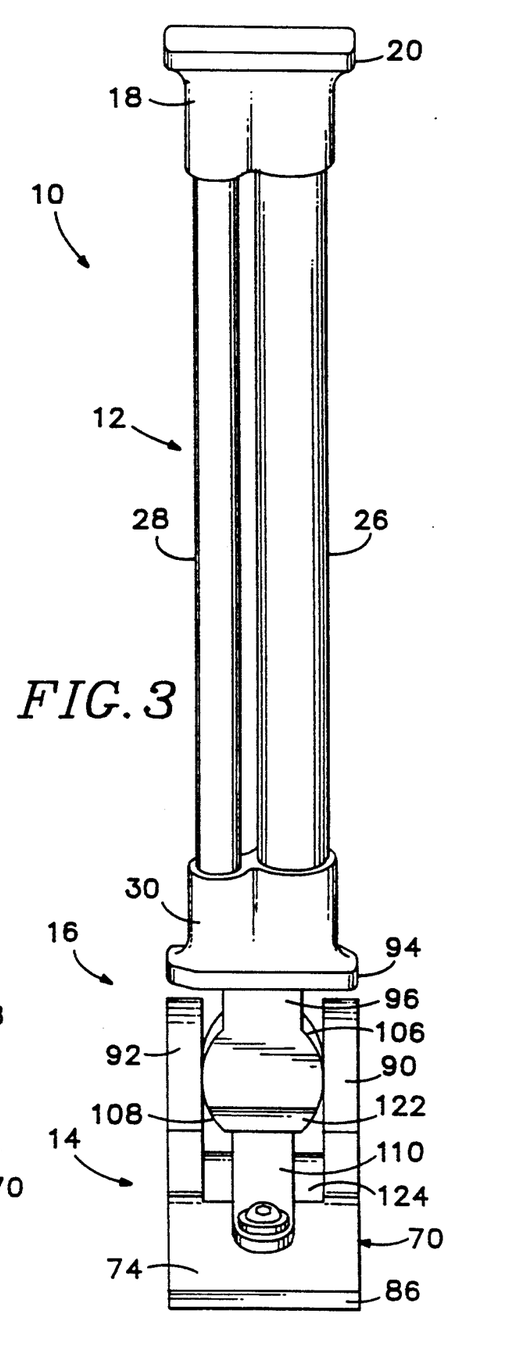
FIG. 3 is a back plan view of the invented limb.

The invented artificial limb is shown generally at 10 in FIGS. 1, 2 and 3. The limb is divided into three sections, an artificial shin 12, an artificial foot 14, and an artificial ankle 16.

Shin 12 includes a first mount 18 positioned below an artificial knee or an amputation socket. An amputation socket is the device that receives an amputated limb and that secures a prosthesis to the limb.

First mount 18 can be connected to an artificial knee or an amputation socket by bolts or any known means. Typically first mount 18 includes a base 20 through which bolts (not shown) would connect to the artificial knee or amputation socket. Alternatively, the first mount 18 can be formed integrally with an artificial knee or an amputation socket. When the first mount is described as positioned below an artificial knee or an amputation socket, that language is meant to describe both situations, where the mount is connected to a knee or socket and where the mount is formed integrally with the knee or socket, as well as other configurations where the mount is below the knee or socket. Of course, first mount 18 can take many different forms and can be constructed from many different materials such as plastic, aluminum or titanium, often depending on the type of knee or socket to which it is connected. First mount 18 can also be connected to a knee or socket off-center for variances in hips, ankles and feet.

First mount 18 includes two sockets 22 and 24. Socket 22 receives a first rod 26 and socket 24 receives a second rod 28. Rods 26 and 28 extend downwardly from the first mount and represent the tibia and fibula respectively of a human shin. Rods 26 and 28 can be any given length to produce a shin of a desired length. Rods 26 and 28 extend downwardly to a second mount 30 having two sockets 32 and 34 which receive rods 26 and 28 respectively.

In the preferred embodiment, rods 26 and 28 are flexible, allowing them to behave more like actual bones. Additionally, rods 26 and 28 have different diameters which also affect the flexibility of each rod.

Even though they are flexible, rods 26 and 28 must be strong enough to support the weight of a user of the artificial shin. Typically, rods 26 and 28 are constructed from polymer or carbon graphite, both of which have some flexibility but which are strong enough to support the weight of a user. Additionally, rods 26 and 28 can be tubes, and the inner diameters of the tubes can be selected to achieve different strengths and flexibilities. Alternatively, aluminum tubes can be used instead of nylon or carbon graphite, but aluminum is less flexible. More than two rods can also be used, depending on the intended application.

The flexibility of rods 26 and 28 allows for torsional or rotary movement of the shin in the direction of arrows 35 in FIG. 2. The ability of the shin to twist slightly creates a more comfortable prosthesis because it reduces the pressure applied to the tissue at an amputation site. That advantage is particularly helpful in fitting a prosthesis to an older amputee. The flexibility of rods 26 and 28 also permit some forward/backward and side-to-side movement. In the embodiment shown in FIGS. 1-3, rod 26 can be thought of as the primary load-bearing rod and rod 28 can be thought of as a stabilizing rod that restricts the flexibility of rod 26. However, both rods bear some weight during use.

Figure 4:
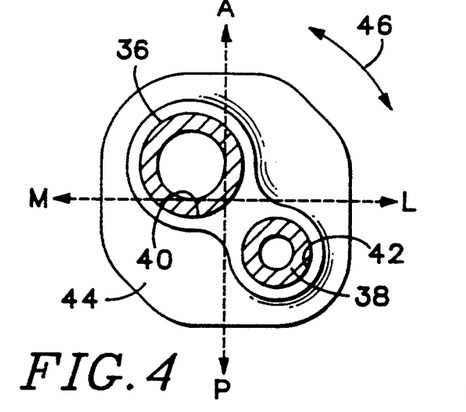
FIGS. 4 through 7 are cross-sectional views of different configurations of rods that may be used in the invented shin, as those rods would be seen looking along a line similar to line 4—4 in FIG. 1.

FIGS. 4 through 7 show different configurations of different rods all of which can be used in the invented shin. FIG. 4 is a simplified cross-sectional view of a shin seen from a line such as line 4—4 in FIG. 1. However, the position of the tubes in FIG. 4 does not correspond to the tubes in FIGS. 1, 2 and 3.

Specifically, FIG. 4 includes a first tube 36 and a second tube 38. The tubes are positioned in sockets 40 and 42 respectively of a mount 44. Mount 44 is similar to second mount 30 in FIG. 1. As can be seen in FIG. 4, tubes 36 and 38 have different outer and inner diameters. Additionally, in FIG. 4 tube 36 is positioned forward and to the left of tube 38. That relationship is similar to the relationship between a tibia and fibular in the right leg of a human, and it allows for different flexibilities in different directions. For example, FIG. 4 includes axes labeled A-P and M-L. The A represents the anterior of the shin, the P represents the posterior, L the lateral and M the medial part of the shin. Different positions of tubes 36 and 38 create different flexibilities along the different axes. Additionally, the torsional or rotary movement of the shin is shown by arrow 46 in FIG. 4.

Figure 5:
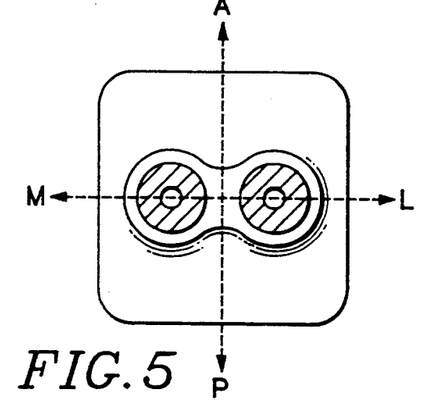

FIG. 5 is similar to FIG. 4 except that it shows a different configuration of tubes. The tubes in FIG. 5 have smaller inner diameters than the tubes in FIG. 4 and the tubes are arranged side by side from the medial side to the lateral side. That orientation allows for greater linear flexibility or, in other words, flexibility from the anterior to the posterior than from the medial to the lateral. The arrangement in FIG. 5 also has a different torsional or rotational flexibility than that shown in FIG. 4.

Figure 6:
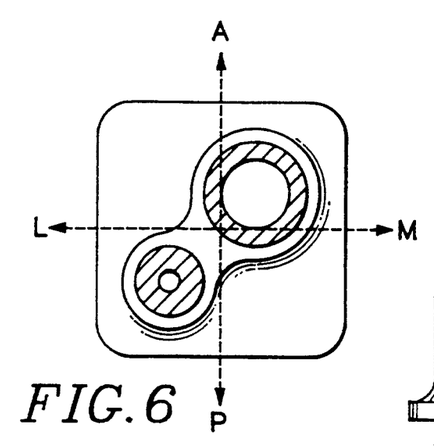
Figure 7:
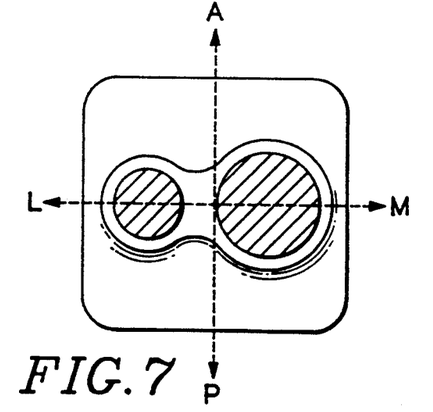

FIGS. 6 and 7 are also similar to FIG. 4 except they show other configurations of rods. In FIG. 6 the rods are tubes and in FIG. 7 they are solid.

Figure 8:
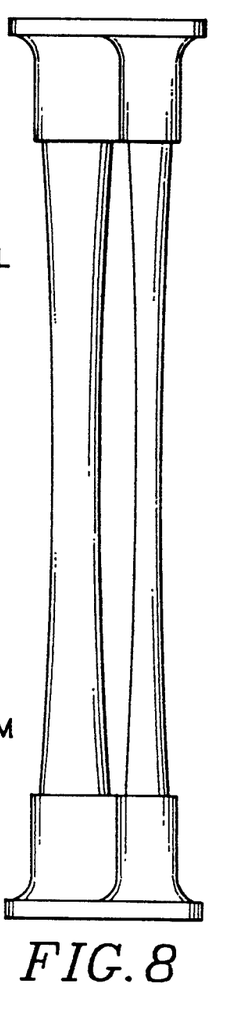
FIG. 8 is a plan view showing different rods that may be used in the invented shin.

FIG. 8 shows still another configuration of rods. Specifically, two rods extend between first and second mounts. Each rod tapers from both ends toward the center, thereby making the rods more flexible around their centers than at their ends. In other words, the rods have varying cross-sectional diameters to create different flexibilities at different points along the rods' lengths.

Figure 9:
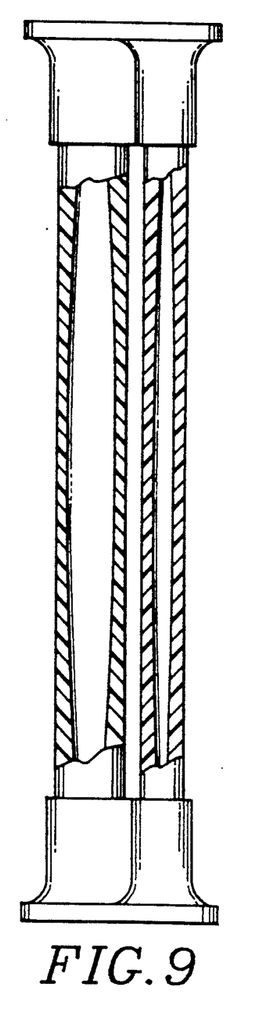
FIG. 9 is a partial sectional view showing tubes with varying inner diameters.

FIG. 9 is similar to FIG. 8 except that it shows tubes with varying cross-sectional inner diameters. The outer diameters of the tubes are constant, but the inner diameters vary to create different flexibilities at different points along the tubes' lengths. In FIG. 9, the cross-sectional inner diameter of the tubes is greatest at the tubes' center, thus making the tubes more flexible around that point.

Returning to FIGS. 1-3, rod 26 can be secured in sockets 22 and 32, and rod 28 can be secured in sockets 24 and 34 by an adhesive, by interior expanding bolts or by a pressure fit. Alternatively, the rods can simply be inserted into the sockets and left loose. Leaving the rods loose in the sockets allows the rods to have greater torsional, rotary, and lateral ranges of movement. To customize a shin for a particular user, some rod ends can be fixed and others can be left loose.

Compression elements such as foam pads 60, 62, 64 and 66 can be placed in sockets 22, 32, 24 and 34, respectively, so that rods 26 and 28 have some vertical movement when the rods are loose in the sockets. The foam pads act as shock absorbers when walking with the invented limb. They also allow for greater stability on uneven ground by allowing, for example, rod 26 to compress pad 62 while rod 28 does not compress pad 66.

The different features described above such as types of rods, positions of rods, fitting of rods in sockets, and the use of compression pads can all be combined to customize the shin for an individual user. Different flexibilities and rotational capabilities also can be adjusted for different applications. For example, flexible, loose-fitting rods can be used for walking while firmer, more solid rods can be used for running.

Figure 10:
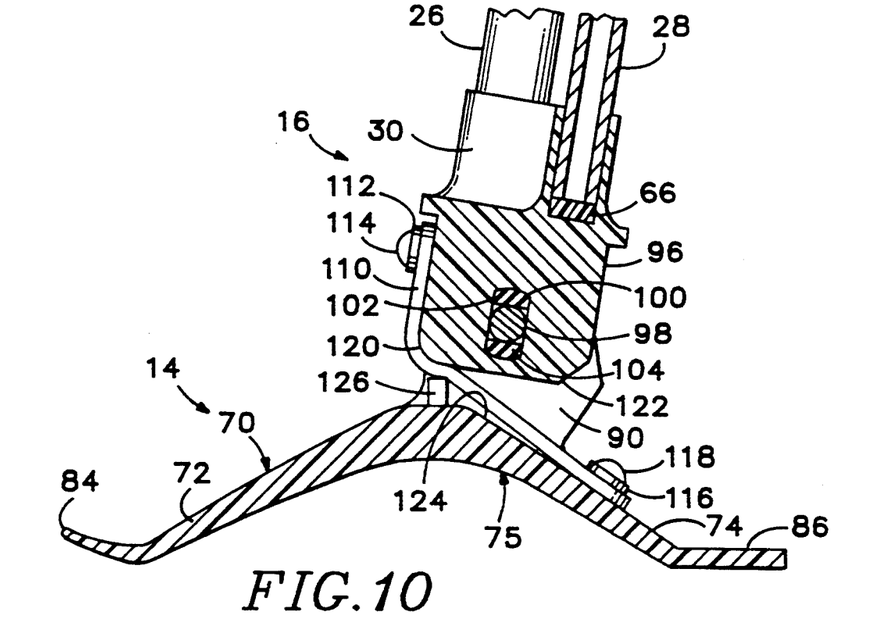
FIG. 10 is a side, sectional view of the foot and ankle shown in FIGS. 1-3 taken along the line 10—10 in FIG. 2.
Figure 13:
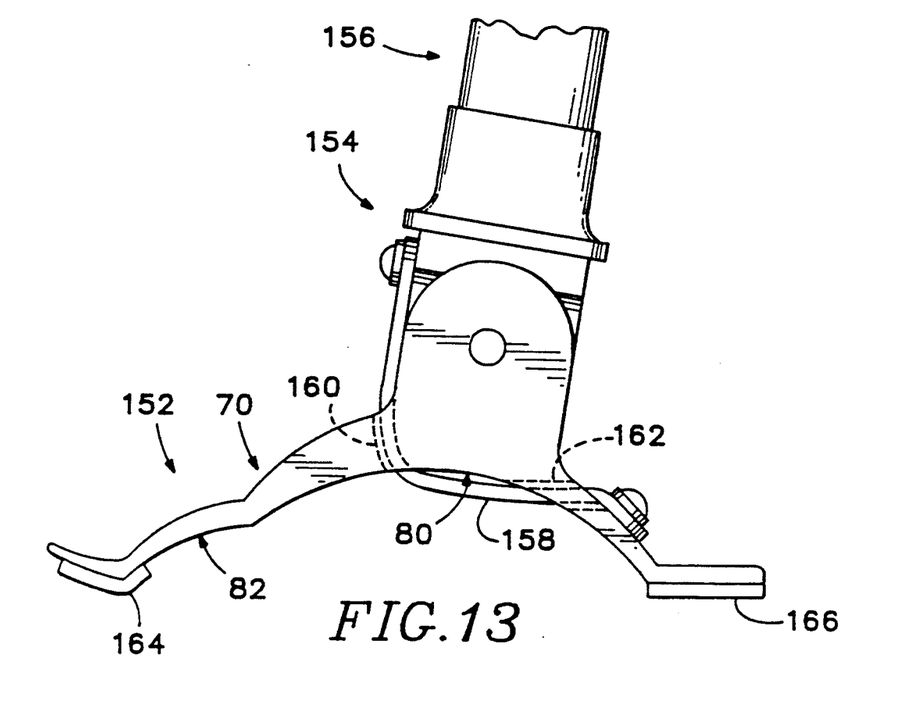

Shin 12 is connected to foot 14 by ankle 16. The foot includes an elongated member 70 with a toe section 72 and a heel section 74. Foot 14 is typically made from glass-reinforced nylon or carbon graphite composite and, as shown in FIGS. 1 and 10, is constructed in an arch 76. The flexibility of glass-reinforced nylon and the arch shape allow for the foot to act as an energy storage spring that absorbs energy on impact and that helps raise the foot during walking. Alternatively, as shown in FIG. 13, the foot may include a double arch, shown as arches 80 and 82. A double arch allows for a stiff upper arch and a flexible lower arch, thereby giving stability to the upper foot while allowing for maximum toe flexibility. The arch in foot 14 also allows the foot to be fitted with normal shoes.

Returning to FIGS. 1 and 2, the toe section 72 of elongate member 70 includes a upturned end 84. The upturned end allows the foot to roll over the toe when weight is on the foot during walking, and it prevents the toe from catching on the ground when the foot is swung forward. The toe section 72 also tapers from the apex of arch 76 toward the upturned toe 84. That tapering creates a sturdy upper section with a flexible toe section.

As can be seen in FIGS. 2 and 3, elongate member 70 is wide enough to provide a stable base for the artificial limb. Additionally, heel section 74 includes a flat end 86 that contacts the ground and supports the foot.

Foot 14 also includes two upwardly extending arms 90 and 92, which are located over arch 76. Upwardly extending arms 90 and 92 support and form part of ankle 16.

As shown in FIGS. 1-3 and 10, second mount 30 includes a base 94 and a downwardly extending section 96 that extends below base 94. Sockets 32 and 34, base 94 and the downwardly extending section 96 of second mount 30 can be formed as a integral unit or as different parts joined together.

Downwardly extending section 96 is positioned between upwardly extending arms 90 and 92 and an axle 98, shown in FIGS. 1 and 10, extends through arm 90, section 96 and arm 92, thereby supporting mount 30 and shin 12. The axle allows mount 30 to rotate around an axis substantially perpendicular to a line between toe section 72 and heel section 74 of foot 14. In other words, shin 12 can rotate around axle 98, back and forth from the toe section to the heel section of foot 14.

Axle 98 passes through tight-fitting bores in arms 90 and 92 and through an oversized bore 100 in downwardly extending section 96, as shown in FIG. 10. Compressible elements such as foam pads 102 and 104 are placed in bore 100, above and below axle 98. Foam pads 102 and 104 allow mount 30 and shin 12 to move laterally, or in other words, to rotate around a second axis. Alternatively, the bores in arms 90 and 92 could be oversized and fitted with foam instead of or in addition to the foam pads in bore 100.

Downwardly extending section 96 is shaped with two outer curved surfaces 106 and 108 which touch the inner surfaces of arms 90 and 92, respectively. When mount 30 and shin 12 move laterally, surface 106 moves against the inner surface of arm 90 and surface 108 moves against the inner surface of arm 92. Of course, the lateral rotation of mount 30 and shin 12 is restricted by the size of bore 100 and by the density of foam pads 102 and 104.

Oversized bore 100 and cushion 104 also allow for a slight vertical displacement of the shin and ankle during walking or running. That vertical displacement absorbs some of the impact when the foot strikes the ground.

An elastic band 110 is attached to the forward surface of downwardly extending section 96 by a washer 112 and a bolt 114. Band 110 extends down the forward surface of section 96, between arms 90 and 92 and under section 96 to the heel section of foot 14, where it is anchored by a washer 116 and a bolt 118. Band 110 restricts the rotation of mount 30 and shin 12 toward the heel section 74 of foot 14. It also pulls mount 30 and shin 12 back to their original positions after rotation of the shin toward the heel section. Section 96 includes a bottom forward edge 120 that is curved to allow band 110 to wrap around it and to extend toward the heel section. Section 96 also has a bottom trailing edge 122 that is cut at an angle to allow clearance of mount 30 during rotation. Additionally, an upper surface 124 of foot 14 is cut to allow the rotation of mount 30 and to allow band 110 to pass under downwardly extending section 96.

A compressible element such as foam pad 126 is mounted on foot 14 on upper surface 124. Pad 126 restricts rotation of mount 30 and shin 12 toward toe section 72. When mount 30 and shin 12 are rotated around axle 98 toward toe section 72, foam pad 126 contacts band 110 which in turn contacts downwardly extending section 96, thereby stopping the rotation of mount 30 and shin 12. The degree and ease of rotation is determined by the durometer (density) and size of foam pad 126. Pad 126 also softens the impact of the foot on the ground by allowing the shin to move forward slightly before the arched foot compresses.

The position of arms 90 and 92, the position of axle 98 and the shape of second mount 30 all work together to properly locate the foot under the shin, for both cosmetic and functional reasons. The construction shown in FIGS. 1-3 puts the foot underneath the knee, not anterior to it. Additionally, mount 30 can position the rods of the shin over the arch to shorten or lengthen the lever arm that flexes the toe section of the foot. The position of the tubes over the arch also affects toe roll-over and the swinging of the foot forward during walking. Rods can also be offset from the center of the heel section to direct weight over the arch. The invented limb is adjustable to meet the requirements set forth above for different gaits.

Figure 11:
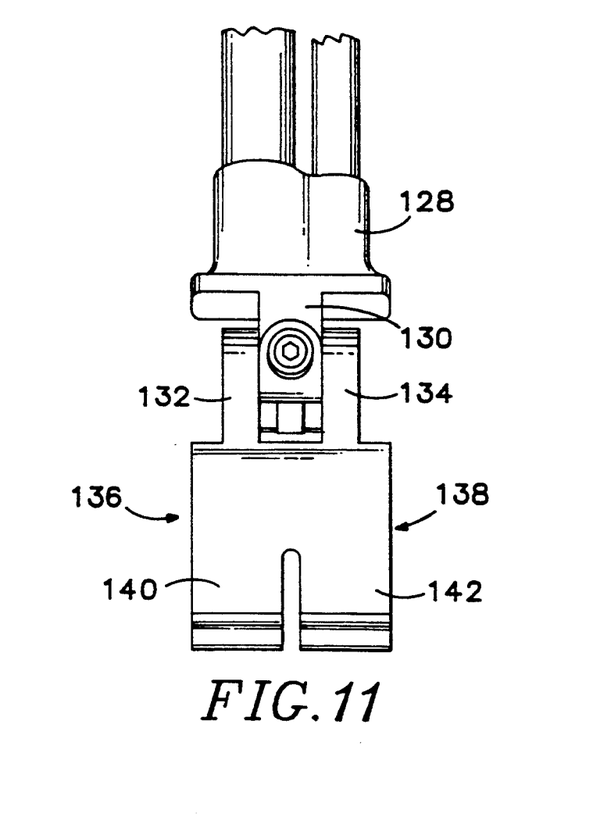
FIG. 11 is a front plan view of another embodiment of the invented ankle and foot.
Figure 12:
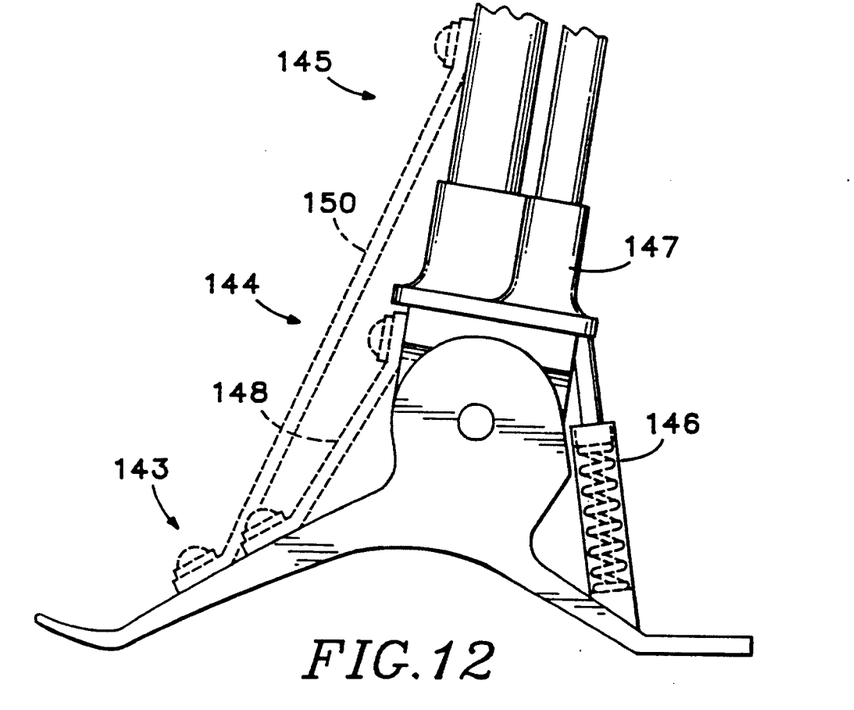
FIGS. 12 and 13 are side plan views showing different embodiments of the invention.

FIGS. 11 through 13 show different embodiments of the invented ankle and foot. Specifically, FIG. 11 shows an ankle that cannot rotate laterally. That embodiment includes mount 128 that has a downwardly extending section 130 which fits snugly between arms 132 and 134 of a foot 136. The snug fit between section 130 and arms 132 and 134 prevents the mount 128 from moving laterally. Additionally, FIG. 11 shows a foot 136 with a toe section 138 cut into two parts, a first part 140 and a second part 142. The cut in toe section 138 allows parts 140 and 142 to flex independently, which is often desired for uneven terrain.

FIG. 12 shows a foot 143 connected to an ankle 144 supporting a shin 145. FIG. 12 shows three different rotation controlling elements connected to the ankle and foot to restrict rotation of the shin toward the heel section of the foot. Any one or any combination of those rotation controlling elements can be used. First, a compression spring 146 is shown connected between the back surface of a mount 147 and the heel section of foot 143. Second, an elastic band 148 is shown in dashed lines connected between the forward surface of mount 147 and the toe section of foot 143. Third, an elastic band 150 is shown in dashed lines connected between the toe section of foot 143 and the shin 148. Each of those embodiments restrict rotation of mount 147 and shin 145 toward the heel section of foot 143.

FIG. 13 shows a foot 152 with a double arch, as described above. Foot 152 is connected to an ankle 154 which supports a shin 156. In FIG. 13, shin 156 is a single tube. An elastic band 158 extends from the forward surface of ankle 154 through an aperture 160 in foot 152, under arch 80 and through a second aperture 162 to anchor on the heel section of the foot. FIG. 13 also shows a pad 164 attached under the upturned toe of foot 152 and a pad 166 under the heel section of the foot. Those pads act as shock absorbers to make a more comfortable foot.

The artificial limb shown in FIGS. 1 through 3 shows an integrated shin, ankle and foot. Alternatively, each section can be constructed separately and joined together. For example, shin 12 could terminate at base 94 of second socket 30. Foot 14 could terminate at upper surface 124 of elongate member 70. Ankle 16 could include arms 90 and 92, which could be bolted to surface 124 of foot 14, as well as downwardly extending section 96, which could be bolted to second mount 30.

Figure 14:
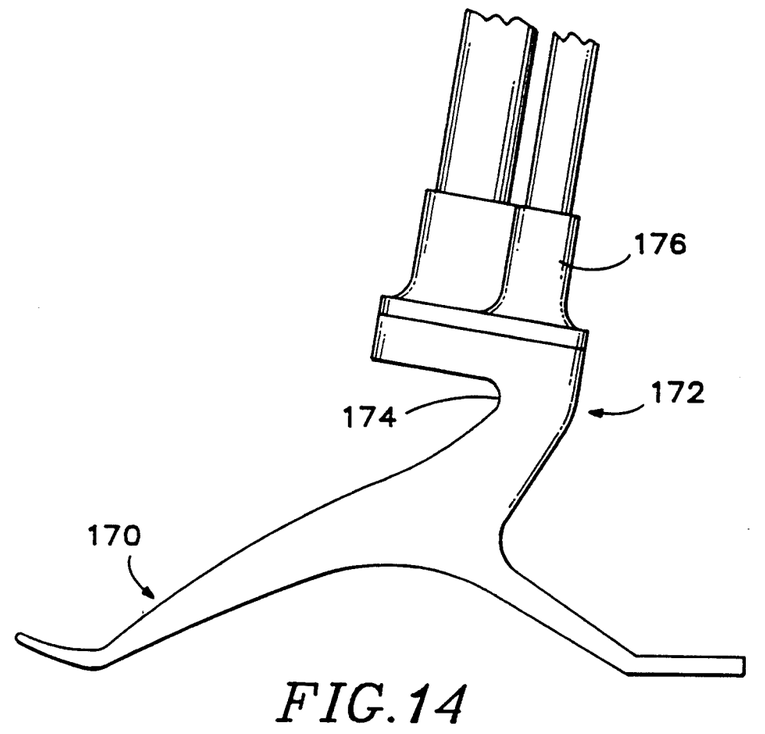
FIG. 14 is a side plan view of a different embodiment of the invention.

FIG. 14 shows another embodiment of the invented foot and ankle. In that embodiment a foot 170 is similar to the previously described feet, except that it has a different ankle section 172. That ankle section includes a substantially U-shaped surface 174 that allows the ankle to flex somewhat in the anterior direction, or toward the toe of the foot. Ankle section 172 also allows for posterior flexion, but it is more difficult to move the ankle in the posterior direction than the anterior direction because of its shape. Ankle section 172 is formed integrally with foot 170 and may also be formed integrally with second mount 176. Alternatively, second mount 176 can be fastened onto ankle section 172. This embodiment allows for greater stability because of its restricted movement in the ankle section. It is also much lighter in weight than other prosthetic ankles. Stiff, stable, light-weight ankles are particularly applicable for older people.

The invented artificial limb can be covered so that it appears more like a human limb by any known method. For example, a flexible foam tube made from polyurethane can surround the shin and ankle. The tube may act as a dust cover as well as a bumper to protect the internal elements. A second foam cover can then be glued to or placed around the first tube. The second foam cover is usually a closed cell foam and would become integral with foot 14. The secondary foam cover can then be colored as desired.

INDUSTRIAL APPLICABILITY

The invented artificial limb is applicable to the prosthesis industry and is specifically designed for lower limb amputees. While the preferred embodiment of the invention has been described, variations and changes may be made without departing from the spirit of the invention.

I claim:

1. A prosthesis comprising:
   an elongate member having a toe section and a heel section;
   a pair of elongate rods which are substantially parallel and spaced from one another;
   a mount coupled to the elongate member for supporting the rods, where the mount is capable of rotation around an axis substantially perpendicular to a line connecting the toe and heel sections of the elongate member where the mount includes a pair of sockets which receive the rods, the rods extending upwardly from the mount to function similarly to a human's tibia and fibula; and
   a rotation controlling element connected to both the mount and the elongate member to restrict rotation of the mount toward the heel section of the elongate member.

2. The prosthesis of claim 1 where the elongate member is flexible.

3. The prosthesis of claim 1 where the elongate member has a first arch in the heel to toe direction.

4. The prosthesis of claim 3 where the elongate member has a second arch in the heel to toe direction.

5. The prosthesis of claim 1 where the elongate member has a thickness that tapers toward the toe section.

6. The prosthesis of claim 1 further comprising a compressible stop that restricts rotation of the mount toward the toe section of the elongate member.

7. The prosthesis of claim 1 where the rotation controlling element is an elastic band.

8. The prosthesis of claim 1 where the rotation controlling element is a compression spring.

9. The prosthesis of claim 1 where the mount is rotatable around a second axis.

10. The prosthesis of claim 9 where the second axis is substantially parallel to a line between the toe and heel sections of the elongate member.

11. The prosthesis of claim 1 where the elongate member includes two upwardly extending arms and the mount includes a downwardly extending section that fits between the two arms, and further comprising an axle that extends between the two arms and through the downwardly extending section to support the mount.

12. The artificial ankle and foot of claim 1 where the sockets are positioned along a line which is oblique relative the length of the elongate member similar to the positioning of a human's tibia and fibula.

13. Artificial ankle and foot comprising:
    an elongate member having a toe section and a heel section;
    a mount coupled to the elongate member for supporting a shin or socket, where the mount is capable of rotation around an axis substantially perpendicular to a line connecting the toe and heel sections of the elongate member; and
    a rotation controlling element connected to both the mount and the elongate member to restrict rotation of the mount toward the heel section of the elongate member;
    where the elongate member includes two upwardly extending arms and the mount includes a downwardly extending section having a forward surface, the downwardly extending section fitting between the two arms, and further comprising an axle that extends between the two arms and through the downwardly extending section to support the mount;
    where the rotation controlling element is an elastic band attached to the forward surface of the downwardly extending section and which extends under the downwardly extending section toward the heel section and anchors on the elongate member.

14. An artificial shin comprising:
    a first mount for positioning below a user's knee;
    a second mount for positioning above an artificial foot; and
    a plurality of rods extending between the first and second mounts, where at least one rod is a load-bearing rod, and where the shin has an anterior side and a posterior side, the rods being mounted along a line which extends obliquely relative to the anterior and posterior sides of the shin, so that the rods are positioned similarly to a human's tibia and fibula bones, respectively.

15. An artificial shin comprising:
    a first mount for positioning below a user's knee;
    a second mount for positioning above an artificial foot; and
    a plurality of flexible rods extending between the first and second mounts, where at least one rod is a load-bearing rod, and where the rods are cylindrical, have different cross-sectional diameters and different flexibilities and are substantially parallel and spaced from one another.

* * * * *